US009254312B2

(12) United States Patent
Ehrenreich et al.

(10) Patent No.: US 9,254,312 B2
(45) Date of Patent: Feb. 9, 2016

(54) METHOD FOR THE TREATMENT AND/OR PROPHYLAXIS OF MULTIPLE SCLEROSIS, AND USE OF ERYTHROPOIETIN FOR THE MANUFACTURE OF A MEDICAMENT FOR THE INTERMITTENT TREATMENT AND/OR INTERMITTENT PROPHYLAXIS OF MULTIPLE SCLEROSIS

(76) Inventors: Hannelore Ehrenreich, Goettingen (DE); Klaus-Armin Nave, Goettingen (DE)

( * ) Notice: Subject to any disclaimer, the term of this patent is extended or adjusted under 35 U.S.C. 154(b) by 2079 days.

(21) Appl. No.: 12/223,197

(22) PCT Filed: Jan. 25, 2007

(86) PCT No.: PCT/EP2007/000640
§ 371 (c)(1),
(2), (4) Date: Jan. 21, 2011

(87) PCT Pub. No.: WO2007/085453
PCT Pub. Date: Aug. 2, 2007

(65) Prior Publication Data
US 2011/0112018 A1 May 12, 2011

(30) Foreign Application Priority Data
Jan. 27, 2006 (DE) .......................... 10 2006 004 008

(51) Int. Cl.
A61K 38/00 (2006.01)
A61K 38/19 (2006.01)
A61K 38/18 (2006.01)

(52) U.S. Cl.
CPC .................................. A61K 38/1816 (2013.01)

(58) Field of Classification Search
None
See application file for complete search history.

(56) References Cited

U.S. PATENT DOCUMENTS

| 5,441,868 | A | 8/1995 | Lin |
| 5,994,127 | A | 11/1999 | Selden et al. |
| 6,528,313 | B1 | 3/2003 | Le Mouellic et al. |
| 6,638,768 | B1 | 10/2003 | Le Mouellic et al. |
| 7,129,267 | B2 | 10/2006 | Renzi et al. |
| 2004/0203153 | A1 | 10/2004 | Le Mouellic et al. |
| 2004/0250301 | A1 | 12/2004 | Le Mouellic et al. |
| 2005/0032682 | A1 | 2/2005 | Asou et al. |
| 2007/0009967 | A1 | 1/2007 | Renzi et al. |
| 2007/0065885 | A1 | 3/2007 | Renzi et al. |

FOREIGN PATENT DOCUMENTS

| EP | 1 295 604 A1 | 3/2003 |
| WO | WO 85/02610 A1 | 6/1985 |
| WO | WO 86/03520 A1 | 6/1986 |
| WO | WO 90/11354 A1 | 10/1990 |
| WO | WO 91/06667 A1 | 5/1991 |
| WO | WO 91/09955 A1 | 7/1991 |
| WO | WO 93/09222 A2 | 5/1993 |
| WO | WO 94/12650 A2 | 6/1994 |
| WO | WO 95/05465 A1 | 2/1995 |
| WO | WO 95/31560 A1 | 11/1995 |
| WO | WO 00/61164 A1 | 10/2000 |
| WO | WO 2006/002646 A2 | 1/2006 |

OTHER PUBLICATIONS

Sattler et al. (Cell Death Differentiation 11: S181-S192, 2004).*
Marcel Leist et al; "Derivatives of Erythropoietin That Are Tissue Protective But Not Erythropoietic"; Science; Jul. 9, 2004; pp. 239-242; vol. 305.
Michael Brines and Anthony Cerami; "Emerging biological roles for erythropoietin in the nervous system"; Nature Reviews; Neuroscience; Jun. 2005; pp. 484-494; vol. 6.
Claudia Bartels et al.; "Recombinant human erythropoietin: novel strategies for neuroprotective/neuroregenerative treatment of multiple sclerosis"; Therapeutic Advances in Neurological Disorders; Nov. 2008; pp. 193-206; vol. 1, No. 3; Sage Publications.
Hannelore Ehrenreich et al.; "Exploring recombinant human erythropoietin in chronic progressive multiple sclerosis"; Brain; Oct. 2007, pp. 2577-2588; vol. 130, No. Part 10; Oxford University Press.

* cited by examiner

*Primary Examiner* — Daniel E Kolker
*Assistant Examiner* — Aditi Dutt
(74) *Attorney, Agent, or Firm* — Marshall & Melhorn, LLC

(57) ABSTRACT

The present invention relates to a method for the treatment and/or prophylaxis of multiple sclerosis, and to the use of erythropoietin for this purpose and for the manufacture of a medicament for the intermittent treatment and/or intermittent prophylaxis of multiple sclerosis.

15 Claims, 7 Drawing Sheets

METHOD FOR THE TREATMENT AND/OR PROPHYLAXIS OF MULTIPLE SCLEROSIS, AND USE OF ERYTHROPOIETIN FOR THE MANUFACTURE OF A MEDICAMENT FOR THE INTERMITTENT TREATMENT AND/OR INTERMITTENT PROPHYLAXIS OF MULTIPLE SCLEROSIS

BACKGROUND OF THE INVENTION

The present invention relates to a method for the treatment and/or prophylaxis of multiple sclerosis and also the use of erythropoietin for this purpose and also for the production of a drug for intermittent treatment and/or intermittent prophylaxis of multiple sclerosis.

With approx. 80 to 110 cases of multiple sclerosis (MS) per 100,000 persons, multiple sclerosis is the most frequent chronic disease of the central nervous system. A third of patients thereby shows a primary or secondary progressive course of the multiple sclerosis, for which no therapy has been available to date. In particular no therapy is available which would achieve an improvement in the symptoms.

Erythropoietin is a glycoprotein produced naturally in the body, having a molecular weight of 34,000 D. It is an essential growth factor for the production of erythrocytes and was isolated for the first time already in 1977.

Erythropoietin has been in frequent clinical use for many years in patients with renal anaemia, in the case of nephrodialysis, in order to obtain fairly large quantities of autologous blood before planned operations, and it also appeared in press headlines as a doping agent.

Erythropoietin thereby proved to be exceptionally well tolerated. There should be mentioned as a relevant side-effect, in particular the often therapeutically desired stimulation of haematopoiesis with polyglobuly as well as arterial hypertension which is rarely to be observed. Both effects can be expected mainly after chronic erythropoietin administration. If required, these can be remedied relatively easily by medicinal treatment or blood-letting. Intolerance reactions or anaphylactic reactions are rarities with erythropoietin. WO 00/61164 discloses the use of EPO for the protection of neuronal tissue, in particular also of the central nervous system. It is mentioned in passing in this document that multiple sclerosis might also be treated with EPO.

There is considered by EPO or erythropoietin in the sense of the present invention and also in WO 00/61164, any erythropoietin, whether native or recombinant, from humans or another mammal, whether in native sequence or even after sequence changes or sequence shortening, any type of erythropoietin analogue, erythropoietin fragments or even substances binding to the erythropoietin receptor or erythropoietin agonists. The definition for erythropoietin or EPO according to WO 00/61164 is adopted in its entirety in the present application. Accordingly, by EPO and by erythropoietin any substance is meant, which can activate EPO-activated receptors in systemic application, i.e. also any type of variants, fragments or analogues. Further useable EPO variants are published for example in the following publications:

Leist et al., Science 2004, Vol. 305, pp. 239-242, WO 86/03520, WO 85/02610, WO 90/11354, WO 91/06667, WO 91/09955, WO 93/09222, WO 94/12650, WO 95/31560, WO 95/05465.

An overview of known EPO variants and analogues which can also be used in their entirety in the present invention and also of their known fields of use appears in Brines and Cerami, Nature Reviews, Neuroscience, June 2005, Vol. 6, pages 484-494.

It is not of particular relevance in the present invention whether the EPO analogues or erythropoietin fragments which are used have a haematopoietic effect or not. This is explained more precisely further on.

WO 00/61164 in fact discloses the use of EPO for the treatment of multiple sclerosis but indicates no experimental data or treatment regime.

BRIEF SUMMARY OF THE INVENTION

It is therefore the object of the present invention to develop the use of erythropoietin for the treatment of multiple sclerosis such that a significant stabilisation or improvement of the symptoms is achieved. This object is achieved by the method according to claim 1 and also the use according to claims 14 and 15. Advantageous developments of the method according to the invention and of the uses according to the invention are given in the respective dependent claims.

DETAILED DESCRIPTION OF THE INVENTION

Figure 1:
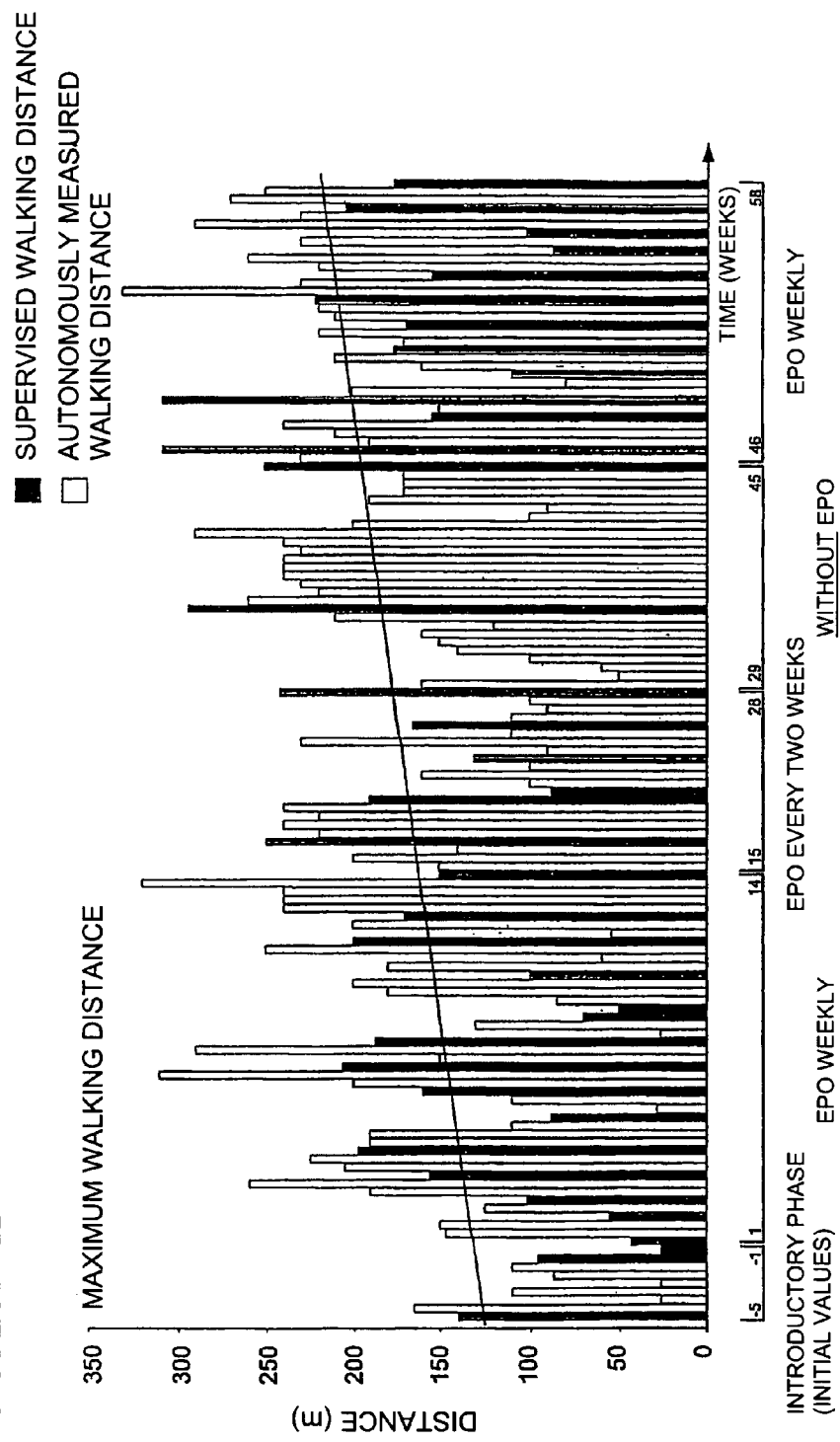
FIG. 1 is a graph showing motor functions with EPO interval treatment.

According to the invention, in the method for the treatment and/or prophylaxis of multiple sclerosis in mammals, in particular in humans, the erythropoietin is now applied intermittently. This means that, with the present invention, an interval treatment is proposed. It is thereby particularly advantageous if the treatment comprises a sequence of periods of time with application of EPO (application period) and periods of time without application of EPO (application-free periods).

The individual periods of time thereby comprise several weeks. A sequence has emerged as particularly advantageous in which each application period lasts 12 to 48 weeks, advantageously 18 to 36 weeks, advantageously 24 to 28 weeks, whilst the application-free periods last 8 to 53 weeks, advantageously 16 to 28 weeks. Within the application periods, the dosage can be varied, for example firstly a period of time with a weekly application and a subsequent period of time with a two-weekly application.

The present invention serves in particular for the use of erythropoietin in a method of this type or the use of erythropoietin for the production of a drug with which the described method can be implemented.

The dosage is thereby respectively in the values described in the claims, particularly advantageously in a dosage range of 5,000 IU to 100,000 IU (international units) per week or per administration.

With the mentioned interval dosage schemes, the result surprisingly is a constant improvement in the clinical symptoms during treatment. The improved level is maintained astonishingly in the interval and the second cycle produces a further improvement.

Surprisingly, an improvement in the symptoms was shown not only in the case of chronic-progressive multiple sclerosis but also in the case of relapsing-remitting multiple sclerosis. In particular in the case of chronic-progressive multiple sclerosis, a deterioration in the symptoms would have been expected during the treatment-free interval. However stabilisation also occurred here.

The interval treatment according to the invention is an innovative approach to the entire concept of neuroprotection which, in the case of EPO with multiple sclerosis, exploits in addition the fact that the result with half-yearly erythropoietin treatment is a latent, desired lack of iron. Since lack of iron can be advantageous in addition for the known neuroprotective EPO effect in chronic inflammatory diseases such as multiple sclerosis, advantageously iron is substituted neither in the treatment nor in the treatment-free phase. The treatment-free phase serves therefore also for slow replenishment of the depleted iron stores, as a result of balanced nutrition.

In particular in the case of use of EPO with haematopoietic effect, the neuroprotective effect is consequently supplemented by the latent lack of iron produced by the EPO treatment.

The effect according to the invention is however also achieved already by using EPO derivatives or variants without haematopoietic effect.

The above explanation relates to the method but the invention is not only directed to the therapeutic method but also to the use of EPO in a method of this type and also the use of EPO for the production of a drug for use in a method of this type.

In the following, a few examples of use according to the invention of erythropoietin-α (commercial name Erypo/Eprex) or erythropoietin-β (commercial name Neorecormon) are given.

FIG. 1 shows the course of the maximum walking distance (prototype of motor function measurement in multiple sclerosis) in a female patient (case example) who had an EPO interval treatment over a period of 58 weeks. As is evident from the Figure, the patient had an introductory phase of in total five weeks in order to determine the baseline values of her walking distance. There followed a weekly administration of EPO over 14 weeks. After the 15$^{th}$ week till the 28$^{th}$ week inclusive, she received EPO every two weeks. From week 29 to 45, a treatment phase was provided, i.e. the patient obtained no EPO. From week 46 to 58, she was again treated weekly with EPO. The illustrated "trend line" shows a constant increase in the maximum walking distance over the total course of examination. This course should be expected in the reverse direction (progressive deterioration in the walking distance) with chronic-progressive MS.

Figure 2:
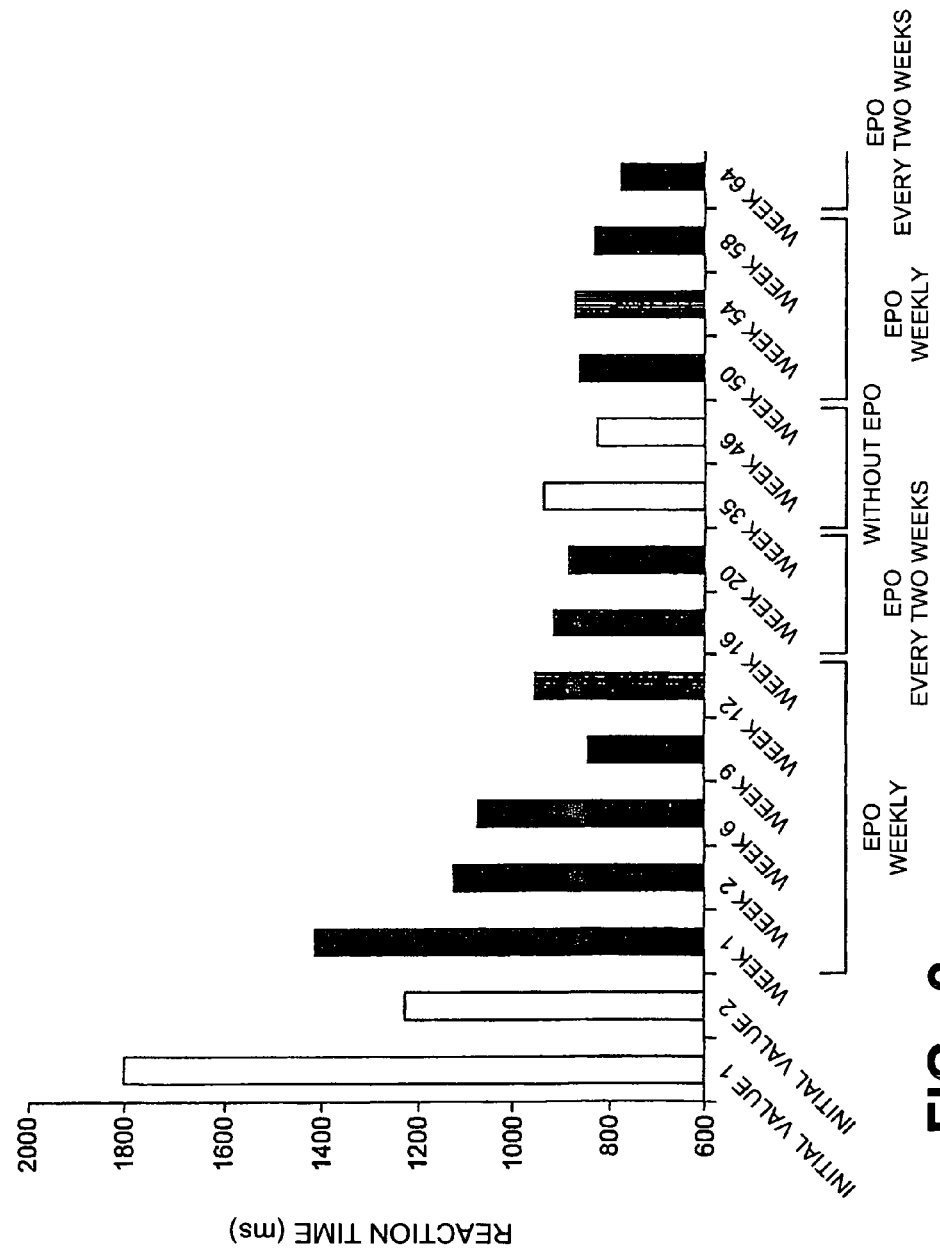
FIG. 2 is a graph showing cognitive improvement: attentiveness.

FIG. 2 shows, with the same patient as in FIG. 1 (EPO interval treatment), an improvement in attention capacity over the various treatment phases without setbacks in performance being able to be observed in the therapy-free interval.

Figure 3:
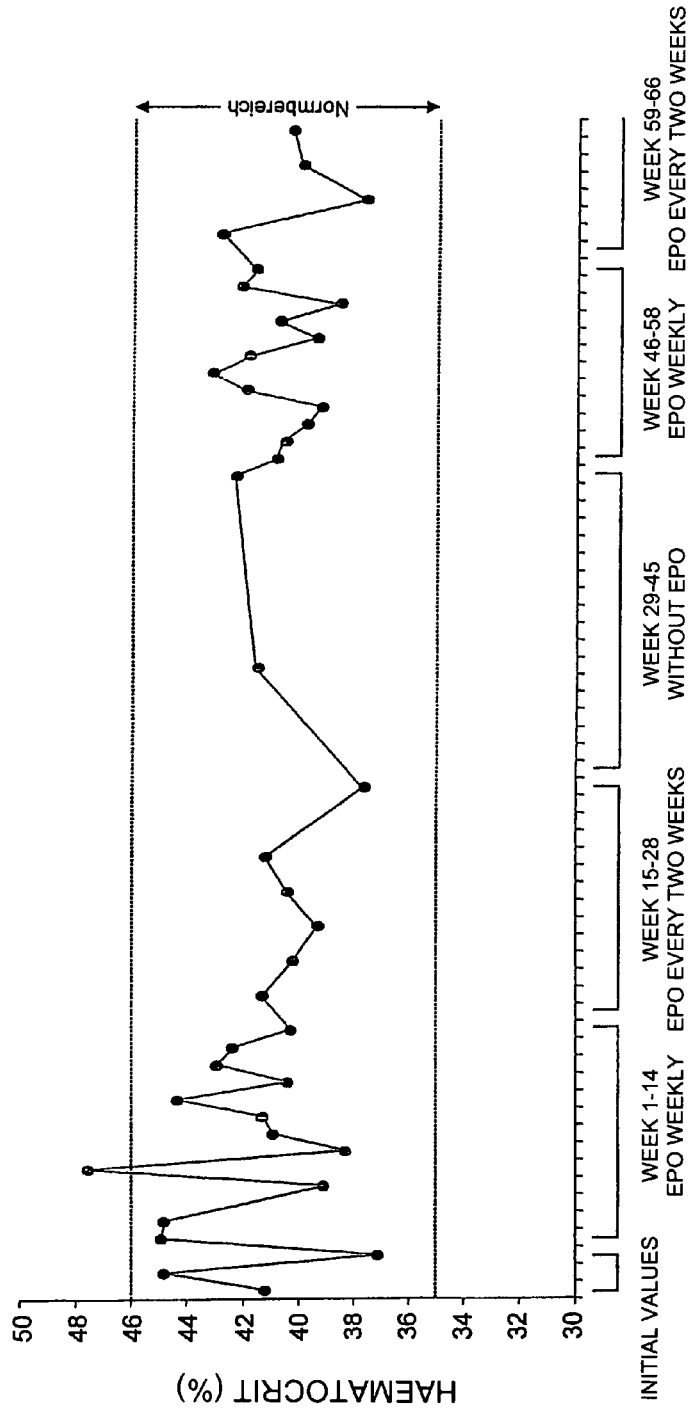
FIG. 3 is a graph showing observations with respect to clinical safety/tolerance: no blood-letting required.

FIG. 3 demonstrates the course of the haematocrit value in the same patient as in FIG. 1 over the entire examination period. The result in this case example is that no value falls outside of the normal range. In this patient, no blood-letting was necessary over the entire treatment duration.

Figure 4:
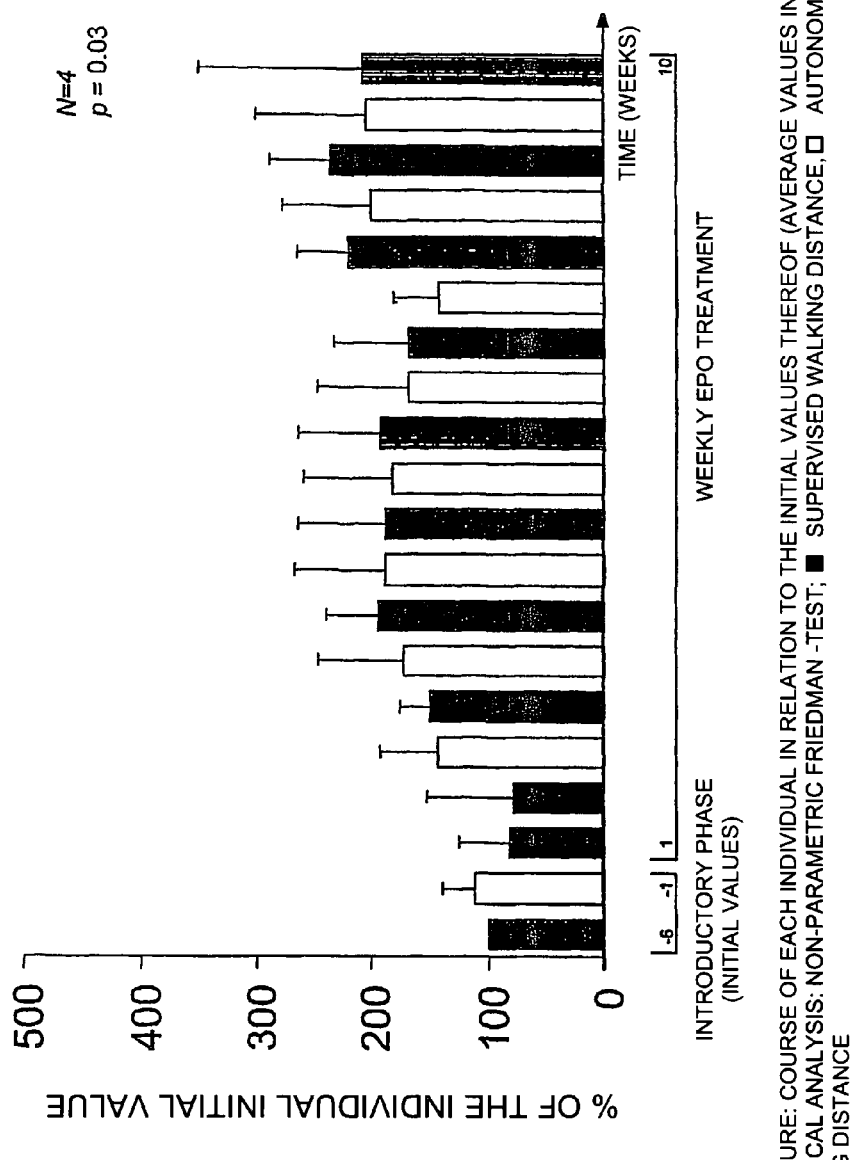
FIG. 4 is a graph showing functional improvement: walking distance.

FIG. 4 summarises the functional improvement in walking distance with four patients who were treated in the same manner as the patient represented in FIG. 1. Over ten weeks of EPO treatment, a significant improvement is already shown.

Figure 5:
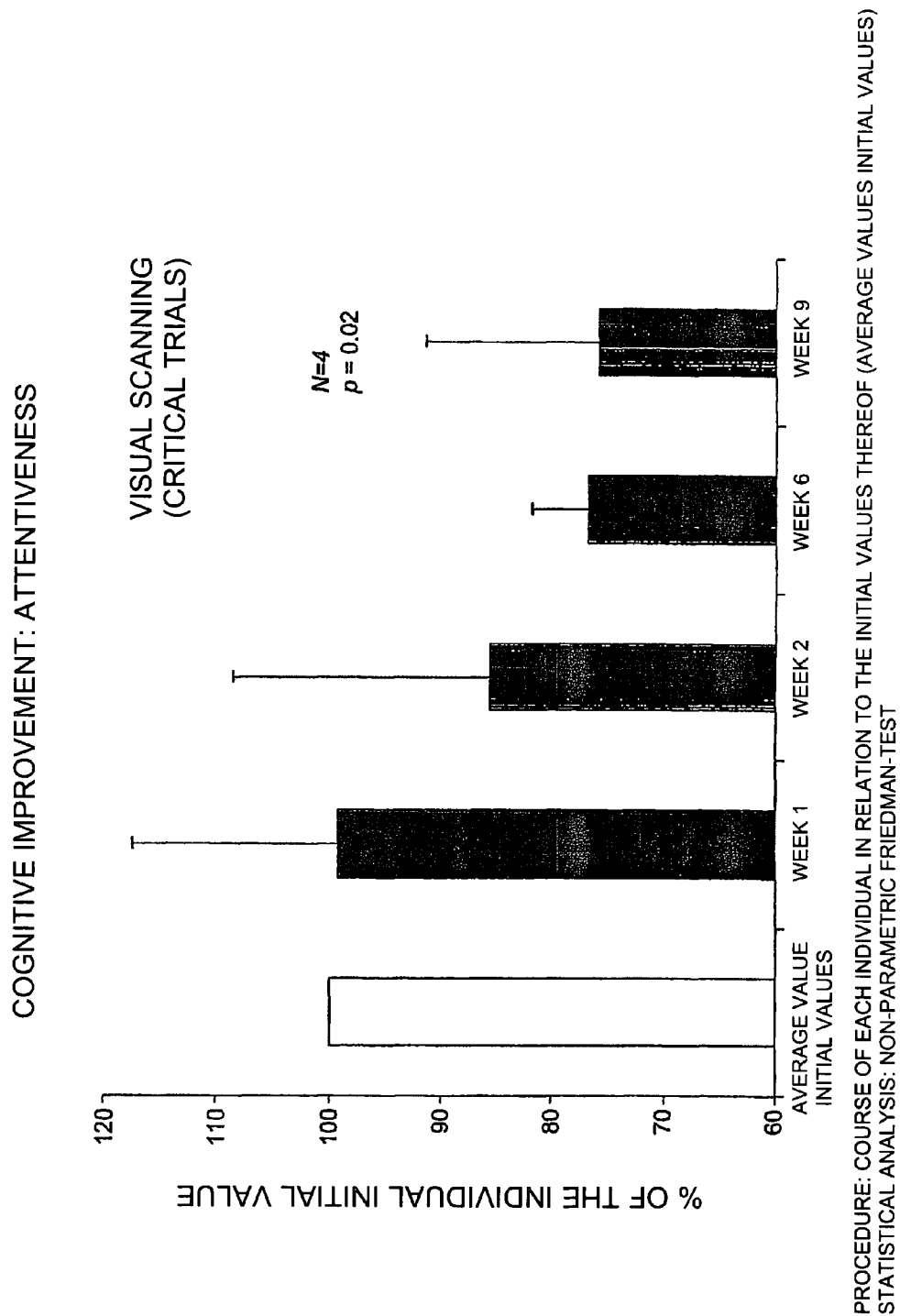
FIG. 5 is a graph showing cognitive improvement: attentiveness.

FIG. 5 shows a summary of the attention capacity (visual scanning) in the four patients shown in FIG. 4 over a period of time of in total nine weeks. The improvement in cognitive performance is significant.

Figure 6:
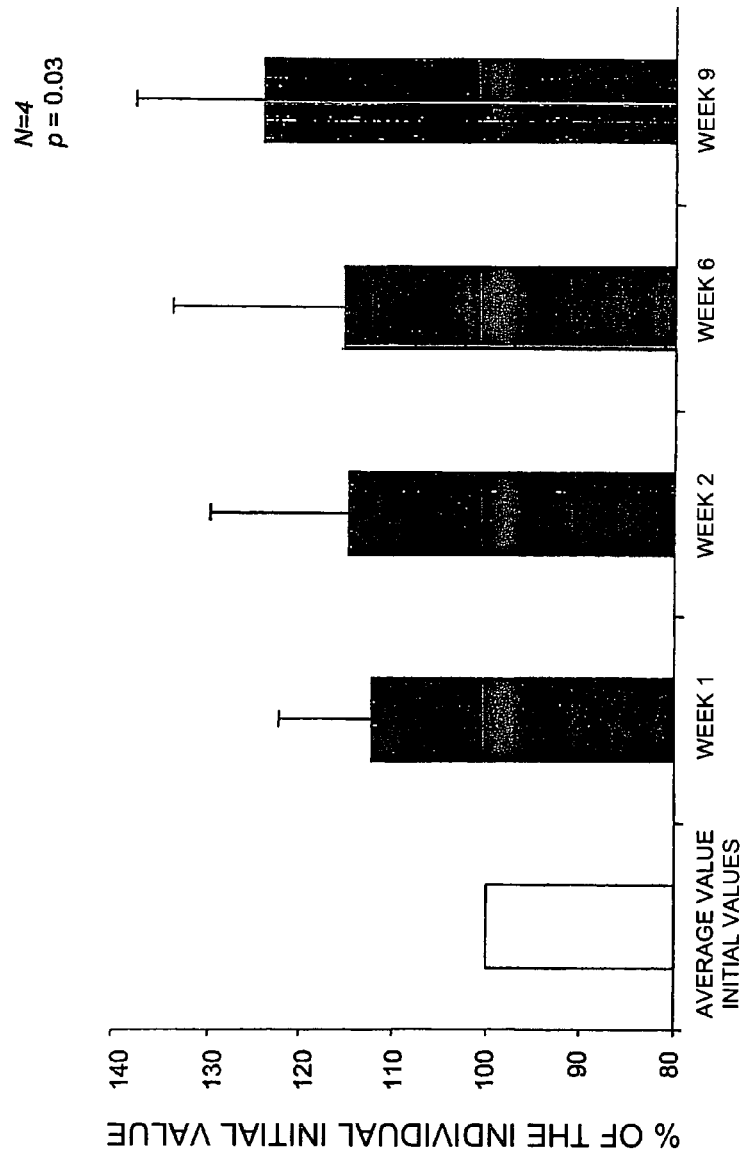
FIG. 6 is a graph showing improvement in fine motoricity: MacQuarrie Tapping Test.

FIG. 6 likewise shows a significant improvement in fine motor-function in the group of four patients, who were represented in FIG. 4, over the first nine weeks of the weekly EPO treatment.

Figure 7:
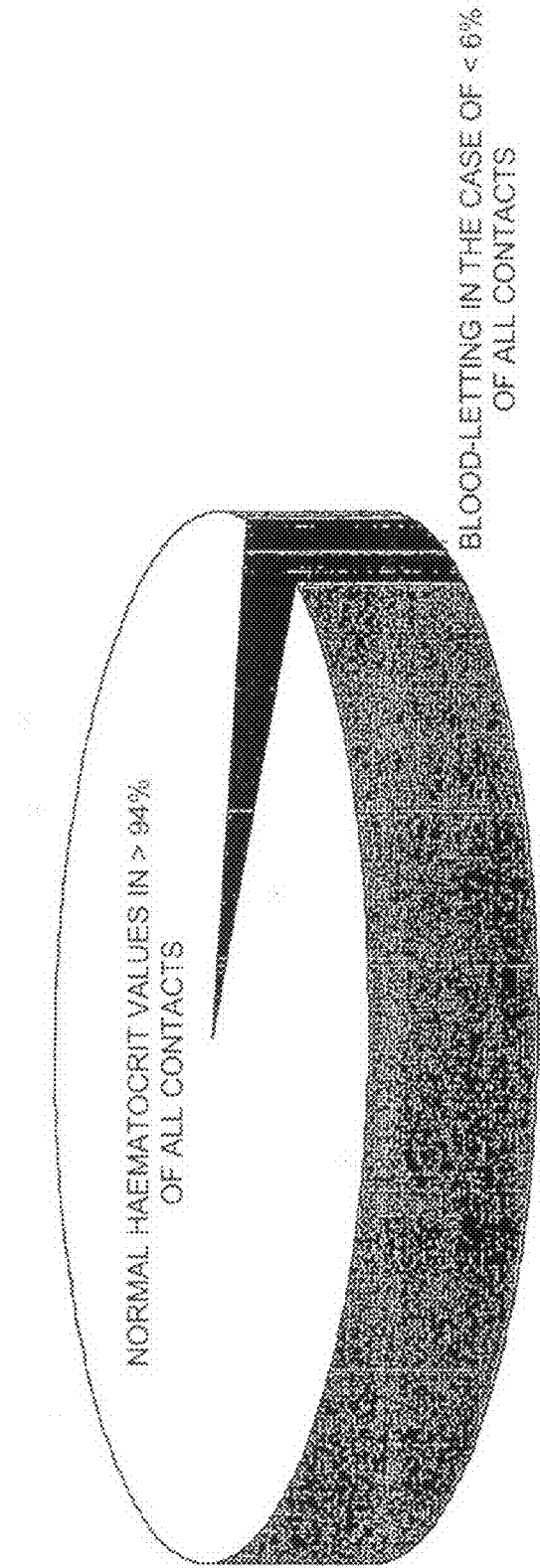
FIG. 7 is a graph showing observations with respect to clinical safety/tolerance (N=4): low incidence of blood-letting during EPO treatment.

FIG. 7 demonstrates, using the group of patients illustrated in FIG. 4, that, with very good clinical safety/tolerance also of the classic (haematopoietic) EPO, the necessity for blood-letting with MS patients is restricted to a small number.

Four patients in total were thereby treated with erythropoietin α (Eprex) or erythropoietin β (Neorecormon).

In summary, it can be established that it was proved that long-term treatment of this type with EPO is well tolerated by the patients.

It was shown in particular that the therapy regime applied improved the motor and cognitive as well as the neurophysiological performance.

The invention claimed is:

1. A method for the treatment and/or prophylaxis of multiple sclerosis in mammals, EPO being applied to the mammal, wherein the EPO is applied in intervals which are interrupted by periods of time in which no EPO is applied, and wherein native or recombinant erythropoietin, an erythropoietin analogue, an erythropoietin fragment, a substance binding to the erythropoietin receptor, an erythropoietin agonist is used as EPO, and wherein the application of the EPO is effected intermittently in at least two application periods with a duration of respectively at least two weeks, wherein application-free periods with a duration of at least two weeks in which no EPO is applied being provided between two application periods.

2. The method according to claim 1, wherein the application is effected parenterally or systemically.

3. The method according to claim 1, wherein the application is effected vascularly, intranasally and/or by inhalation.

4. The method according to claim 1, wherein the application is effected intravenously, subcutaneously and/or intramuscularly.

5. The method according to claim 1, wherein the mammal is a human.

6. The method according to claim 1, wherein EPO is used in native form, synthetic and/or recombinant form with or without sequence changes or sequence variants.

7. The method according to claim 1, wherein an EPO with or without haematopoietic effect is used as EPO.

8. The method according to claim 1, wherein the EPO is given in a dose of 1,000 IU to 200,000 IU per application.

9. The method according to claim 1, wherein an application period lasts 12 to 48 weeks.

10. The method according to claim 1, wherein an application-free period lasts 8 to 53 weeks.

11. The method according to claim 1, wherein at least one of the application periods comprises a first and a subsequent second partial periods, EPO being applied weekly in the first partial period and EPO being applied every two weeks in the subsequent second partial period.

12. The method according to claim 1, wherein the EPO is given in a dose of 5,000 IU to 100,000 IU per week.

13. The method according to claim 1, wherein an application period lasts 18 to 36 weeks.

14. Method according to claim 1, wherein an application period lasts 24 to 28 weeks.

15. Method according to claim 1, wherein an application-free period lasts 16 to 28 weeks.

\* \* \* \* \*